US012766163B2

(12) United States Patent
Chin et al.

(10) Patent No.: US 12,766,163 B2
(45) Date of Patent: Oct. 20, 2026

(54) METHOD OF TREATING BREAST CANCER IN A SUBJECT BY INHIBITING TUBB2B

(71) Applicant: City University of Hong Kong, Kowloon (HK)

(72) Inventors: Yuet Ming Rebecca Chin, Kowloon (HK); Jianyang Hu, Kowloon (HK); Qingling He, Kowloon (HK)

(73) Assignee: City University of Hong Kong, Kowloon (HK)

(*) Notice: Subject to any disclaimer, the term of this patent is extended or adjusted under 35 U.S.C. 154(b) by 784 days.

(21) Appl. No.: 18/148,466

(22) Filed: Dec. 30, 2022

(65) Prior Publication Data

US 2024/0216416 A1 Jul. 4, 2024

(51) Int. Cl.
*A61K 31/712* (2006.01)
*A61P 35/00* (2006.01)
*C12N 15/113* (2010.01)

(52) U.S. Cl.
CPC ............ *A61K 31/712* (2013.01); *A61P 35/00* (2018.01); *C12N 15/1135* (2013.01); *C12N 2310/14* (2013.01); *C12N 2310/531* (2013.01)

(58) Field of Classification Search
CPC .............. A61K 31/712; A61K 31/7105; A61K 31/713; C12N 15/1135; C12N 2310/14; C12N 2310/531
See application file for complete search history.

(56) References Cited

PUBLICATIONS

Jaglin, Xavier Hubert, et al. ("Mutations in the β-tubulin gene TUBB2B result in asymmetrical polymicrogyria." Nature genetics 41.6 (2009): 746-752.2015).*
An, Dong Sung, et al. ("Efficient lentiviral vectors for short hairpin RNA delivery into human cells." Human gene therapy 14.12 (2003): 1207-1212).*
Liu et al. ("Upregulation of MAPK10, TUBB2B and RASL11B may contribute to the development of neuroblastoma." Molecular medicine reports 20.4 (2019): 3475-3486.).*
Aravindan et al. ("Emerging therapeutic targets for neuroblastoma." Expert opinion on therapeutic targets 24.9 (2020): 899-914).*
Nami et al, ("Genetics and expression profile of the tubulin gene superfamily in breast cancer subtypes and its relation to taxane resistance." Cancers 10.8 (2018)).*
C. Döring et al. "A novel immunohistochemical classifier to distinguish Hodgkin lymphoma from ALK anaplastic large cell lymphoma" Modern Pathology (2014) 27, 1345-1354.
G. Cederquist et al. "An inherited TUBB2B mutation alters a kinesin-binding site and causes polymicrogyria, CFEOM and axon dysinnervation" Human Molecular Genetics, 2012, Vo. 21, No. 26, 5484-5499, doi: 10.1093/hmg/dds393.

(Continued)

*Primary Examiner* — Kimberly Chong
(74) *Attorney, Agent, or Firm* — Renner, Kenner, Greive, Bobak, Taylor & Weber

(57) ABSTRACT

This invention provides a designed short hairpin RNA (shRNA) containing RNA interference (RNAi) molecules. RNAi molecules hybridizes to a certain sequence of mRNA of TUBB2B. This invention develops a method of inhibiting TUBB2B expression in mammalian cell and a method of treating or controlling a cancer or tumor mediated by TUBB2B overexpression, including the step of administering a shRNA into a subject.

12 Claims, 9 Drawing Sheets

Specification includes a Sequence Listing.

(56) References Cited

PUBLICATIONS

Z. Wang et al. "Associated analysis of PER1/TUBB2B with endometrial cancer development caused by circadian rhythm disorders" Medical Oncology (2020) 37:90, doi: 10.1007/s12032-020-01415-4.
A. Waks et al. "Breast Cancer Treatment a Review" JAMA vol. 321, No. 3, Jan. 22, 2019, pp. 288-300.
The Cancer Genome Atlas Network "Comprehensive molecular portraits of human breast tumors" Nature vol. 490 Oct. 4, 2012, pp. 61-70 doi: 10.1038/nature11412.
G. Ciriello et al. "Comprehensive Molecular Portraits of Invasive Lobular Breast Cancer" Cell (2015) 163, pp. 506-519. doi: 10.1016/j.cell.2015.09.033.
K. Dreval et al. "Gene Expression and DNA Methylation Alterations During Non-alcoholic Steatohepatitis-Associated Liver Carcinogenesis" 2019 Front. Genet. vol. 10 doi: 10.3389/fgene.2019.00486.
B. Lehmann et al. "Identification of human triple-negative breast cancer subtypes and preclinical models for selection of targeted therapies" J Clin Invest. 2011; 121(7):2750-2767. doi: 10.1172/JCI45014.
M. Breuss et al. "Tubulins and brain development—The origins of functional specification" Molecular and Cellular Neuroscience 84 (2017) 58-67. doi: 10.1016/j.men.2017.03.002.
J. Liu et al. "Upregulation of MAPK10, TUBB2B and RASL11B may contribute to the development of neuroblastoma" Molecular Medicine Reports 20: 3475-3486, 2019. doi: 10.3892/mmr.2019.10589.

* cited by examiner

METHOD OF TREATING BREAST CANCER IN A SUBJECT BY INHIBITING TUBB2B

SEQUENCE LISTING

The Sequence Listing file entitled "MKCP671SL(XML)" having a size of 35,488 bytes and a creation date of Nov. 30, 2022 that was filed with the patent application is incorporated herein by reference in its entirety.

TECHNICAL FIELD

This invention relates to a designed short hairpin RNA (shRNA) for treating or controlling a cancer or tumor mediated by TUBB2B overexpression. Particularly, this invention relates to a method of inhibiting expression of TUBB2B to treat or control a cancer or tumor by designed shRNA containing RNA interference (RNAi) molecules.

BACKGROUND

Breast cancer is the most common cancer affecting women worldwide. Despite recent improvements in breast cancer mortality rates, this disease remains the second most common cause of death in women. Breast cancer is categorized into three major subtypes: luminal, HER2+/ER−, and basal-like. The majority of basal-like tumors (~70%) are triple-negative (ER−/PR−/HER2−). Chemotherapy, usually with high toxicity, is the main treatment option for basal-like, triple-negative breast cancer (TNBC), thus, there is an urgent clinical need to identify novel therapeutic targets for this aggressive subtype.

TNBC is currently the only primary breast tumor subtype without effective targeted therapy, and as a consequence, generally affected patients have poor outcomes. Chemotherapy, usually with life-threatening toxicity, is the main treatment option for TNBC.

TUBB2B (NIH Gene ID: 347733 (https://www.ncbi.nlm.nih.gov/gene/347733)), a β-tubulin isoform primarily expressed in the brain in the embryonic stage, plays a crucial role in axon guidance. Loss-of-function mutations in TUBB2B result in congenital neuronal disorders. In adults, TUBB2B is mainly expressed in neuroglia, with minimal expression in the breast. In the context of cancer, recent studies report overexpression of TUBB2B in liver cancer, neuroblastoma, and Hodgkin lymphoma. Furthermore, higher TUBB2B expression in a subpopulation of endometrial cancer patients is associated with a poorer prognosis. However, the functional role of TUBB2B in the pathogenesis of cancer is yet to be identified.

Because of poor prognosis and a more aggressive phenotype, there is an urgent clinical need to identify novel molecular therapeutic targets and approaches to improve the survival of TNBC patients and treatment methods, therefore.

SUMMARY OF THE INVENTION

An embodiment of the present invention relates to a short hairpin RNA (shRNA) for inhibiting TUBB2B expression includes a RNA interference (RNAi) molecule, where the RNAi molecule hybridizes to a target sequence on an mRNA of TUBB2B gene.

An embodiment of the present invention relates to a method of inhibiting TUBB2B expression, including the step of administering a shRNA to a cell.

An embodiment of the present invention also relates to a method of treating or controlling a cancer or tumor mediated by TUBB2B overexpression, including the step of administering an effective amount of a shRNA to a subject.

An embodiment of the present invention also relates to a pharmaceutical composition including a shRNA.

Without intending to be limited by theory, it is believed that the present invention may provide a shRNA for inhibiting TUBB2B expression further including the reverse complementary sequence of the RNAi molecule. The present invention may provide a shRNA for inhibiting TUBB2B expression including a sequence of 5'-CCGG-RNAi molecule-CTCGAG-reverse complementary sequence of the previous RNAi molecule-TTTTTG-3' and 5'-AATTCAAAAA [SEQ ID No. 20]-RNAi molecule-CTCGAG-reverse complementary sequence of the previous RNAi molecule-3'. The present invention may provide a shRNA for inhibiting TUBB2B expression including a RNAi molecule of SEQ ID No. 1-11. The present invention may further provide a method of inhibiting TUBB2B expression by introducing a lentiviral vector expressing the shRNA in the cell. The present invention may provide a method of inhibiting TUBB2B expression by introducing a lentiviral vector, including a sequence that encodes the shRNA and a suitable promoter for expressing the shRNA. The present invention may provide a method of inhibiting TUBB2B expression in a mammalian cell by the shRNA. The present invention may provide a method of inhibiting TUBB2B expression further including the step of administering a RNAi molecule delivered by gold nanoparticles, where the RNAi molecule of SEQ ID NO. 12-15. The present invention may further provide a method of treating or controlling a cancer or tumor mediated by TUBB2B overexpression by injecting a lentiviral vector that expresses the RNAi molecule therein into the subject. The present invention may provide a method of treating or controlling a cancer or tumor mediated by TUBB2B overexpression further including the step of administering a RNAi molecule delivered by gold nanoparticles, where the RNAi molecule of SEQ ID NO. 12-15. The present invention may further provide a method of treating or controlling breast cancer, endometrial cancer, liver cancer, neuroblastoma and Hodgkin lymphoma by administering the shRNA. The present invention may further provide a method of treating or controlling triple-negative breast cancer by administering the shRNA. The present invention may further provide a pharmaceutical composition further including an effective amount of an additional agent of PI3K/Akt pathway inhibitors, CDK4/6 inhibitors, MEK inhibitors, paclitaxel and cisplatin.

This invention demonstrates that TUBB2B is a critical regulator for the growth of TNBC. Without intending to be limited by theory, it is believed that this shRNA approach against TUBB2B could show greater therapeutic efficacy with less toxicity compared to chemotherapy.

This invention is directed to novel shRNA containing RNAi molecule that inhibits TUBB2B expression. The designed shRNA includes a specific RNAi molecule and its reverse complementary sequence. The RNAi molecules comprise a nucleotide sequence of 21 nucleotides in length that is complementary to a part of the TUBB2B gene. This invention is also directed to the inhibition of TUBB2B overexpression by the designed shRNAs. The invention relates to methods for treating cancers caused by elevated expression of TUBB2B. This invention is also directed to the treatment of breast cancer in a subject, particularly triple-negative breast cancer, with shRNA containing various TUBB2B RNA interference (RNAi) constructs with gene silencing activities, thereby inhibiting the expression of TUBB2B.

Figure 1A:
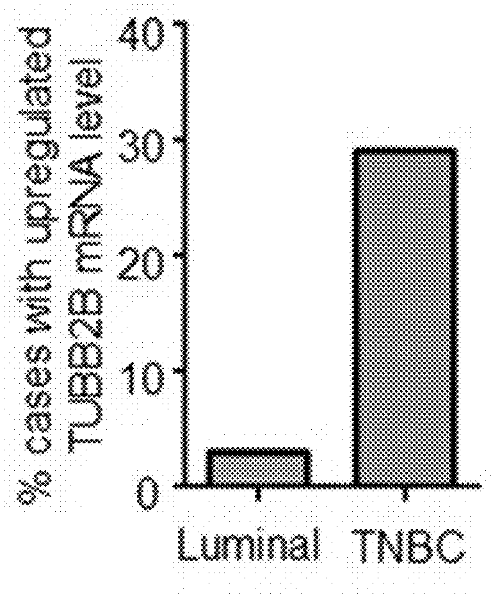
FIG. 1A is a graph showing the percentage of cases with TUBB2B mRNA upregulation in luminal breast tumors and TNBCs, using a dataset from The Cancer Genome Atlas (n=310).

The figures herein are for illustrative purposes only and are not necessarily drawn to scale.

DESCRIPTION OF THE PREFERRED EMBODIMENTS

Unless otherwise specifically provided, all tests herein are conducted at standard conditions which include a room and testing temperature of 25° C., sea level (1 atm.) pressure, pH 7, and all measurements are made in metric units. Furthermore, all percentages, ratios, etc. herein are by weight, unless specifically indicated otherwise. Data quantifications are expressed as mean±s.e.m. The asterisks indicate significant differences at P<0.01, *P<0.001.

It is understood that unless otherwise specifically noted, the materials compounds, chemicals, etc. described herein are typically commodity items and/or industry-standard items available from a variety of suppliers worldwide.

An embodiment of the present invention relates to a short hairpin RNA (shRNA) for inhibiting TUBB2B expression includes a RNA interference (RNAi) molecule, where the RNAi molecule hybridizes to a target sequence on an mRNA of TUBB2B gene.

Without intending to be limited by theory, it is believed that the shRNA designed in the present invention inhibits TUBB2B expression in cells. TUBB2B overexpression is found in liver cancer, neuroblastoma, and Hodgkin lymphoma. Furthermore, higher TUBB2B expression in a subpopulation of endometrial cancer patients is associated with a poorer prognosis. The present invention demonstrates that TUBB2B is a critical regulator for the growth of TNBC and designs a shRNA approach against TUBB2B. The designed shRNA shows greater therapeutic efficacy with less toxicity than chemotherapy. The shRNA, including 21-bp RNAi molecules, can significantly decrease the expression of TUBB2B. In addition, the depletion of TUBB2B induces apoptosis of breast cancer cells. These significant results indicate that inhibiting the overexpression of TUBB2B is an effective and promising approach to treating cancers or tumors mediated by TUBB2B.

In an embodiment herein, the shRNA further includes the reverse complementary sequence of the RNAi molecule.

In an embodiment herein, the shRNA includes a sequence selected from the group consisting of 5'-CCGG-RNAi molecule-CTCGAG-reverse complementary sequence of the previous RNAi molecule-TTTTTG-3', 5'-AATTCAAAAA [SEQ ID No. 20]-RNAi molecule-CTCGAG-reverse complementary sequence of the previous RNAi molecule-3' and a combination thereof.

In an embodiment herein, the RNAi molecule includes a sequence selected from the group of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11 and a combination thereof. SEQ ID NO. 1-11 are 21-nucleotide-long DNA sequences. These 21-bp molecules are the optimal length for loading onto the RNA-induced silencing complex (RISC), for activating the mechanism to degrade the targeted mRNA of TUBB2B.

Another embodiment herein, a method of inhibiting TUBB2B expression, including the step of administering a shRNA to a cell.

In an embodiment herein, the administration step further includes an introduction of a lentiviral vector expressing the shRNA in the cell. A lentiviral vector can get into human tumor cells with high efficiency. Therefore, an effective amount of shRNA could be expressed using this method In an embodiment herein, the lentiviral vector includes a sequence that encodes the shRNA and a suitable promoter for expressing the shRNA. A suitable promoter is required for driving the expression of a sufficient amount of RNAi molecules in order for it to function in tumor cells. A suitable promoter that contains sequence features allows regulatory element binding and initiation of transcription. pLKO.1 vector contains a human U6 promoter that efficiently drives shRNA expression.

In an embodiment herein, the cell is a mammalian cell.

Another embodiment herein, a method of treating or controlling a cancer or tumor mediated by TUBB2B overexpression, including the step of administering an effective amount of a shRNA to a subject.

In an embodiment herein, the administration step further includes the step injecting a lentiviral vector that expresses the shRNA therein into the subject. Injection is an effective way to deliver lentiviral vectors to the tumor cells.

In an embodiment herein, the method of inhibiting TUBB2B expression and method of treating or controlling a cancer or tumor mediated by TUBB2B overexpression further include the step of administering a RNAi molecule delivered by gold nanoparticles, where the RNAi molecule includes a sequence selected from the group of SEQ ID NO. 12, SEQ ID NO. 13, SEQ ID NO. 14, SEQ ID NO. 15 and a combination thereof. In these embodiments, SEQ ID NOS. 12 and 14 are sense strands and SEQ ID NOS. 13 and 15 are anti-sense strands which complementarily pair with SEQ ID NOS. 12 and 14, respectively, separately via covalent bonds. In various embodiments, once the nanoparticles get into cells, sequences 13 and 15 are released from the nanoparticles and bind to TUBB2B mRNA, thereby blocking its expression. As will be apparent, only the sense strands (SEQ ID NOS. 12 and 14) need to be modified. SEQ ID NOS. 12-15 are siRNA sequences. and are, therefore, RNA molecules.

In an embodiment herein, the cancer is selected from the group of breast cancer, endometrial cancer, liver cancer, neuroblastoma, Hodgkin lymphoma and a combination thereof. Overexpression of TUBB2B is suspected in these diseases.

In an embodiment herein, the cancer overexpresses TUBB2B, such as triple-negative breast cancerTUBB2B is significantly overexpressed in triple-negative breast cancer.

In an embodiment herein, the pharmaceutical composition further includes an effective amount of an additional agent selected from the group of a PI3K/Akt pathway inhibitor, a CDK4/6 inhibitor, a MEK inhibitor, paclitaxel, cisplatin, and a combination thereof.

Figure 1B:
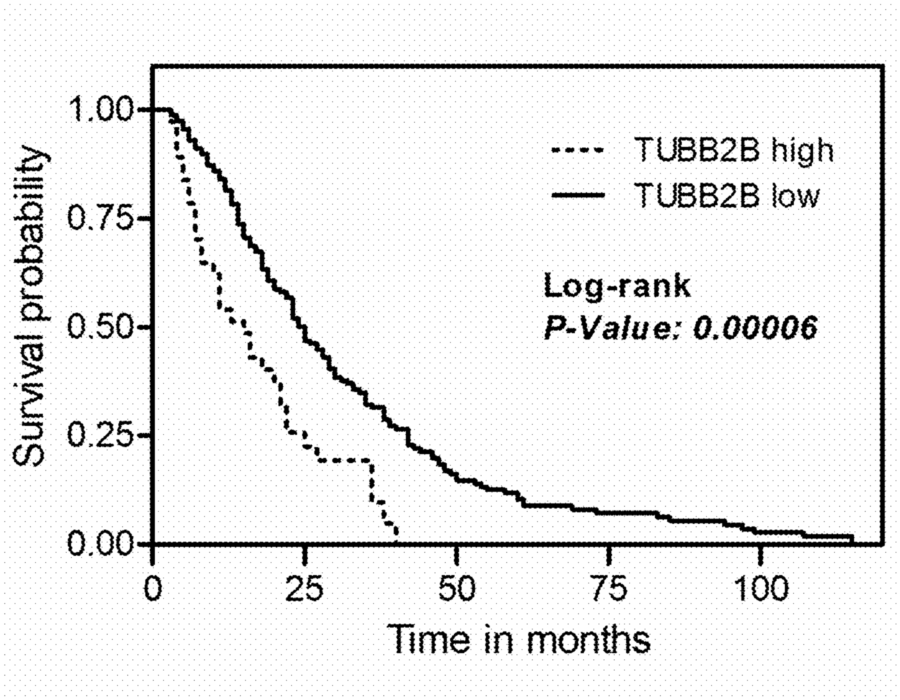
FIG. 1B is a graph showing the survival probability in months of breast cancer patients with high and low expression of TUBB2B.

Turning to the figures, FIG. 1A shows that TUBB2B mRNA expression in TNBC cases is significantly higher, which is 29%. In contrast, 3% of luminal breast tumor cases show an upregulated TUBB2B mRNA level. FIG. 1B shows that increased expression of TUBB2B in breast tumors is significantly associated with shorter distant metastasis-free survival in breast cancer patients (GSE12276; n=202). Accordingly, it is believed that the survival probability of patients with a low TUBB2B expression is about 50% at the 25th month, but 25% for those with a high TUBB2B expression. Therefore, increased expression of TUBB2B is highly likely relevant to the death of TNBC patients.

Figure 2A:
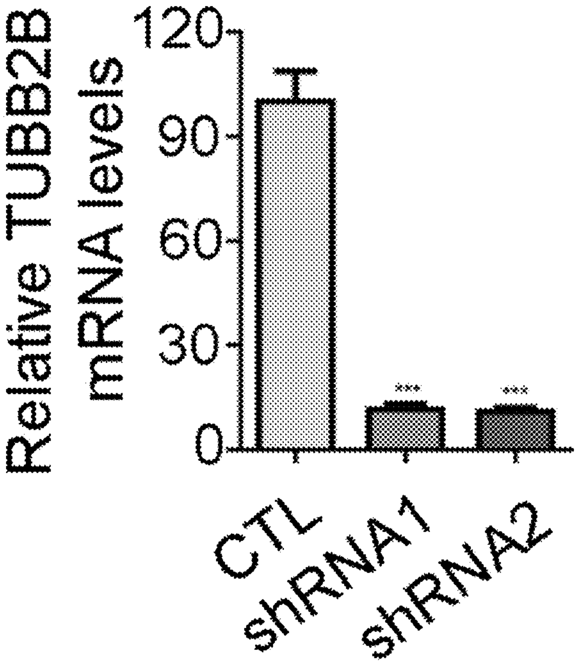
FIG. 2A is a graph showing the relative TUBB2B mRNA levels of BT549 cells infected with control, shRNA1 and shRNA2.

FIG. 2A shows a shRNA lentiviral system for knocking down TUBB2B expression of BT549 cells infected with TUBB2B shRNA or control (CTL) vector for 2 days followed by RT-PCR analysis. The result shows a significant depletion of TUBB2B mRNA with two distinct shRNAs in the TNBC BT549 cell line.

Figure 2B:
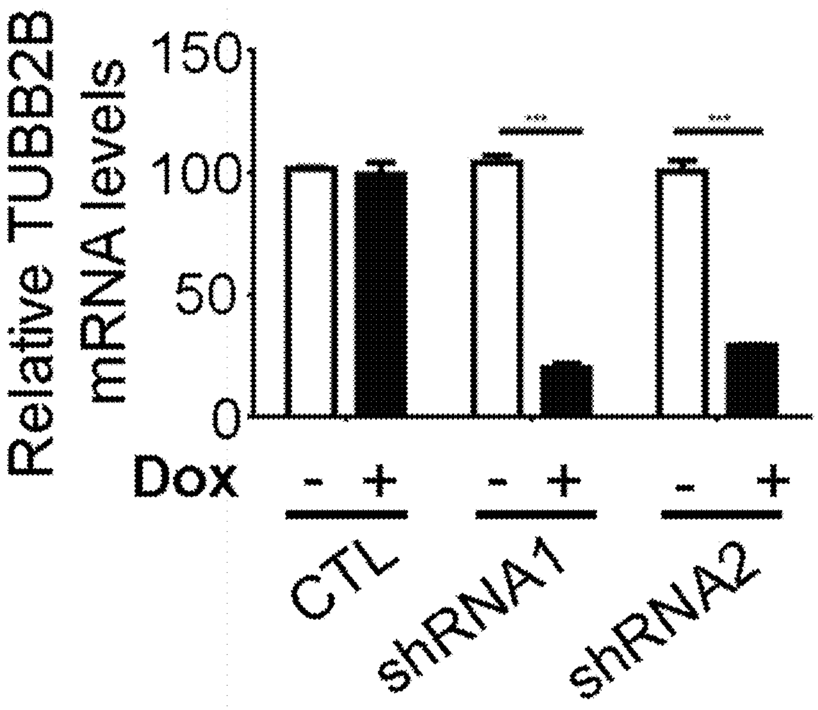
FIG. 2B is a graph showing the relative TUBB2B mRNA levels of doxycycline-treated BT549 cells infected with control, shRNA1 and shRNA2.

FIG. 2B shows the tet-on shRNA systems for depleting TUBB2B in BT549 cells treated with 100 ng/ml doxycycline for 7 days, followed by RT-PCR or Immunoblotting. The result illustrates that the relative TUBB2B mRNA levels significantly decrease in the shRNA groups with doxycycline. It demonstrates that the shRNA lentiviral system effectively knocks down TUBB2B expression.

Figure 3:
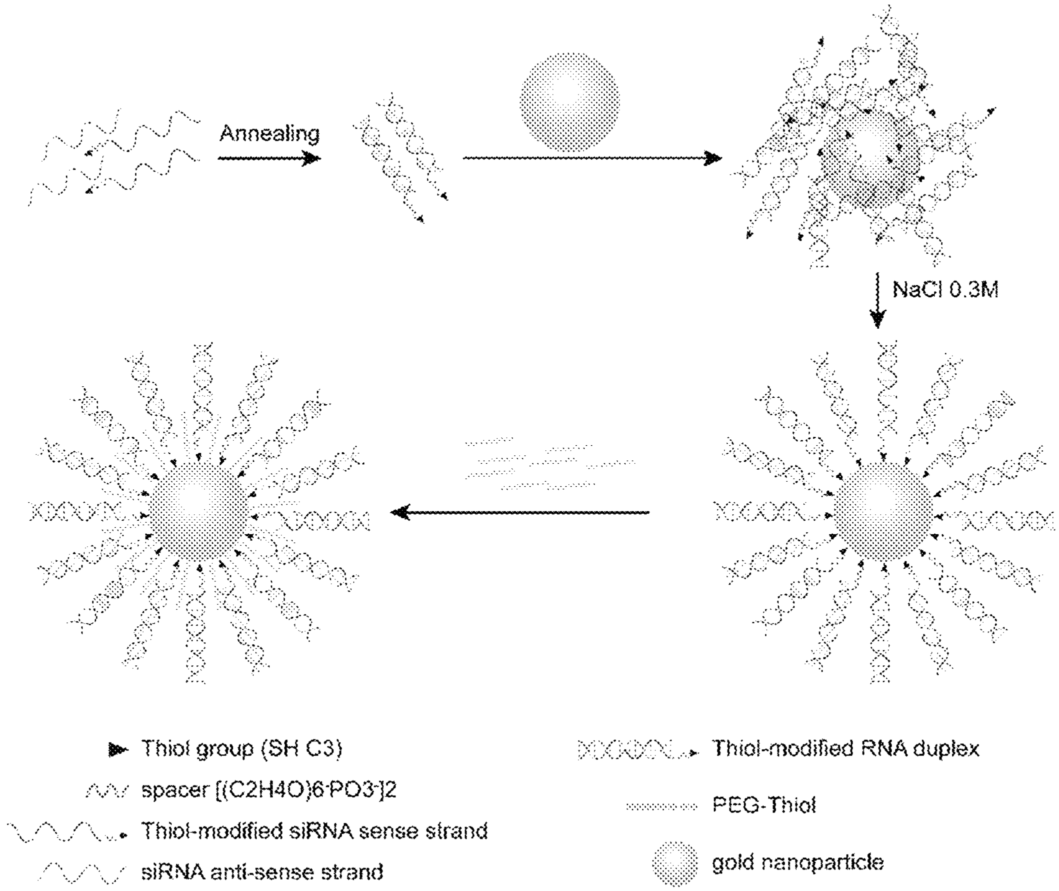
FIG. 3 is a diagram showing the preparation of gold nanoparticles functionalized by RNAi molecules.

FIG. 3 shows the preparation of gold nanoparticles functionalized by RNAi molecules.

Figure 4A:
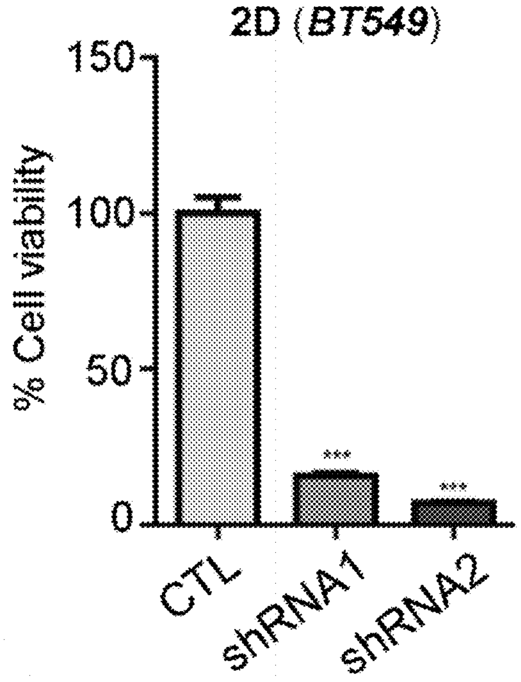
FIG. 4A is a graph showing the cell viabilities of BT549 cells containing CTL, TUBB2B shRNA 1 and TUBB2B shRNA2 in a 2D cell titer-Glo assay.
Figure 4B:
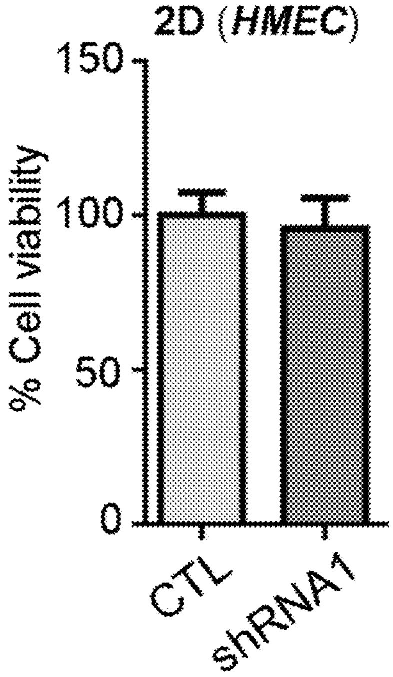
FIG. 4B is a graph showing the cell viability of HMEC cells containing CTL and TUBB2B shRNA 1 in a 2D cell titer-Glo assay.

FIG. 4A shows a 2D cell titer-Glo assay of BT549 cells containing CTL, TUBB2B shRNA1, and TUBB2B shRNA2. FIG. 4B shows a 2D cell titer-Glo assay of HMEC cells containing CTL or TUBB2B shRNA1. The result indicates that silencing TUBB2B can dramatically reduce the 2D cell viability of BT549 but has no effect on HMEC.

Figure 4C:
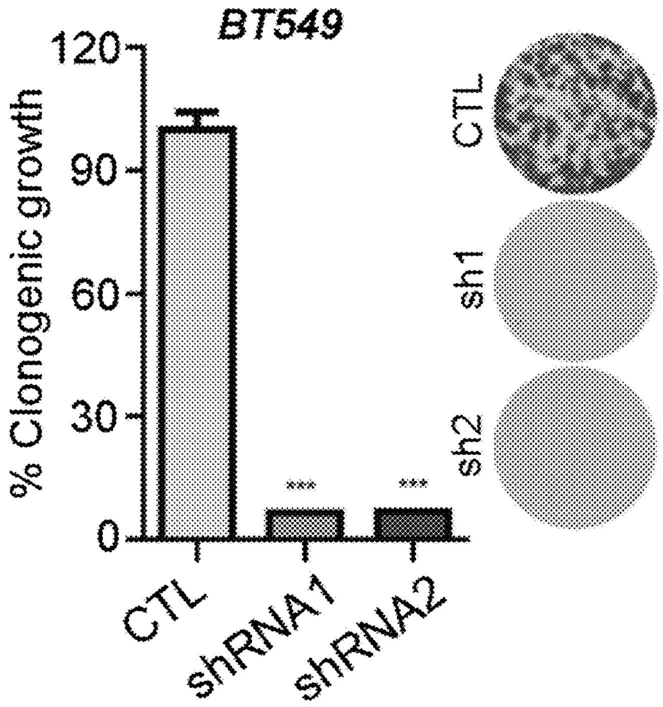
FIG. 4C is a graph and pictures showing the clonogenic growth of BT549 cells with CTL, shRNA1 and shRNA2.
Figure 4D:
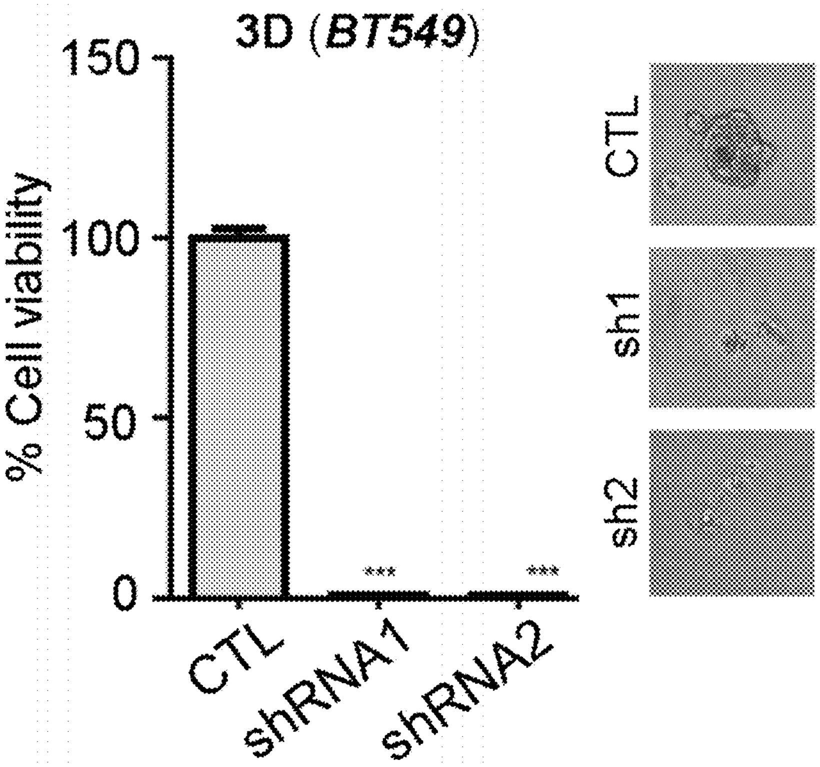
FIG. 4D is a graph and pictures showing the 3D-spheroid cell viabilities of BT549 cells with CTL, shRNA1 and shRNA2.

FIG. 4C shows that the clonogenic growth of BT549 cells with shRNAs decreases markedly compared to the control. The result indicates that TUBB2B depletion inhibits the colony formation ability of BT549 cells. FIG. 4D shows the 3D cell titer-Glo assay where the cell viability of BT549 cells containing CTL or TUBB2B shRNA grown in 3D cultures for 7 days. The result indicates that the cell viability of BT549 cells with shRNAs decreases markedly compared to the control. TUBB2B knockdown significantly decreases the 3D-spheroid cell viability and growth of BT549 cells.

Figure 4E:
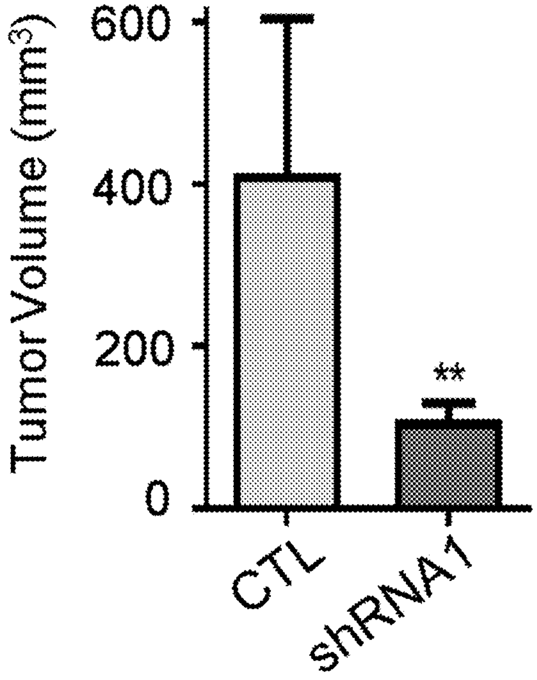
FIG. 4E is a graph showing the tumor volumes of mice injected with MDA-MB-468 cells with CTL and shRNA1.

FIG. 4E shows that tumor volume on Day 60 of the mice injected with MDA-MB-468 cells containing TUBB2B shRNA is about 100 $mm^2$, which is much smaller than 100 $mm^2$ of the control group. The result shows that TUBB2B knockdown decreases the 3D-spheroid cell viability and growth of BT549 cells.

Figure 5A:
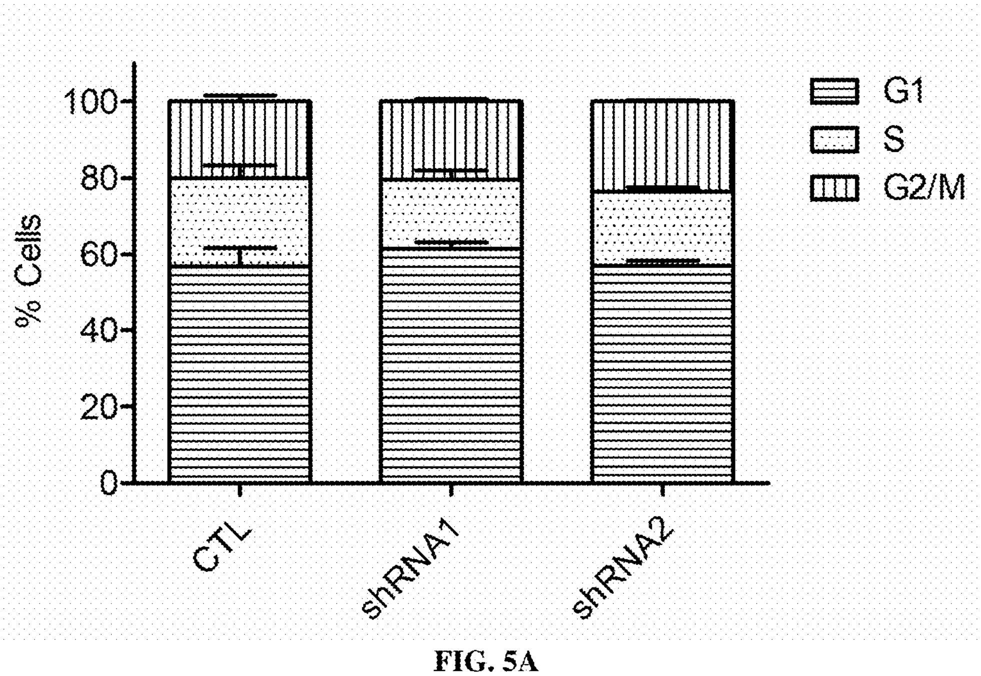
FIG. 5A is a graph showing the cell cycles of BT549 cells containing TUBB2B shRNA1, TUBB2B shRNA2 and an empty vector subjected to flow cytometry after PI staining.

FIG. 5A is the flow cytometry result of PI-stained BT549 cells containing TUBB2B shRNAs and an empty vector. The result shows the cell cycles of BT549 with control and knockdown TUBB2B are similar.

Figure 5B:
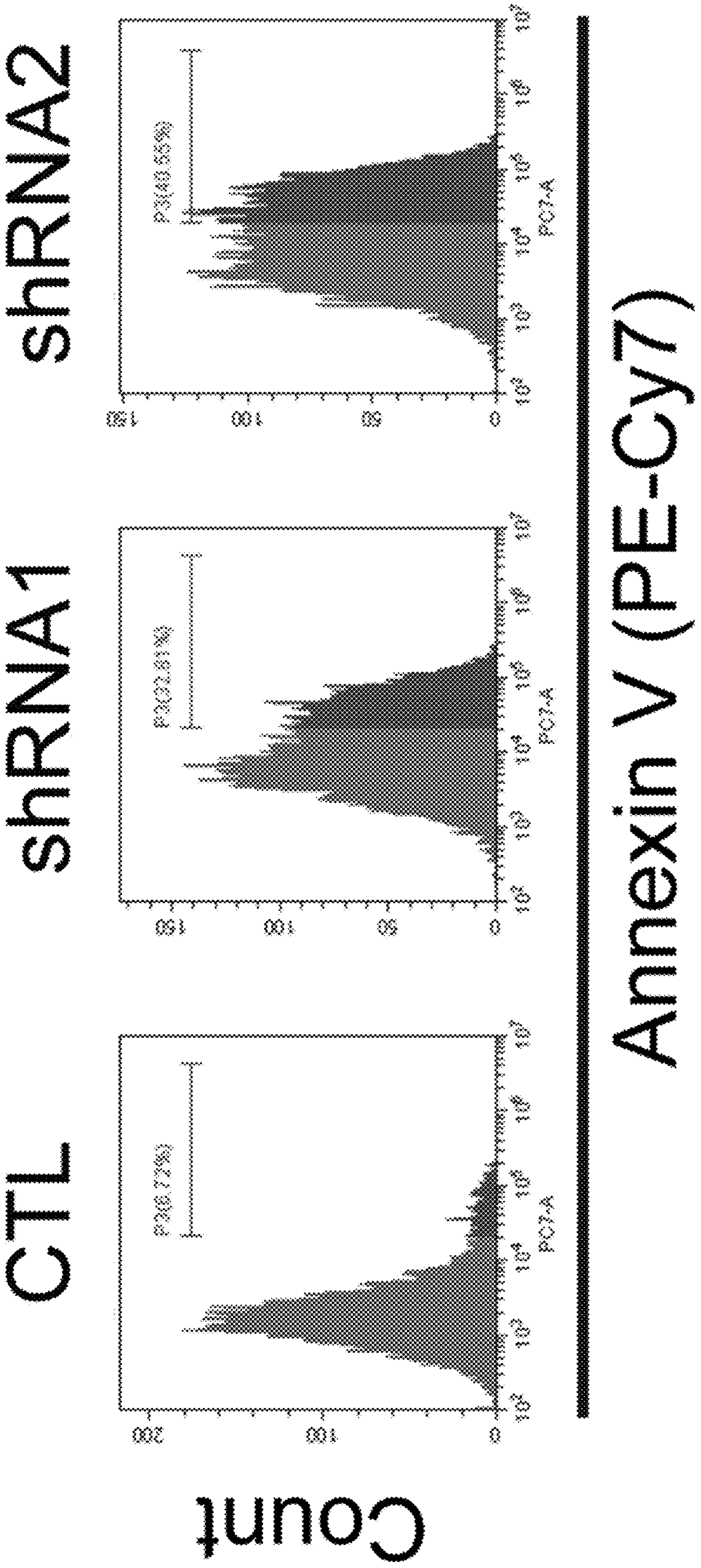
FIG. 5B is the cell counting of BT549 cells containing empty vector, TUBB2B shRNA1 and shRNA2 subjected to flow cytometry after annexin V staining.
Figure 5C:
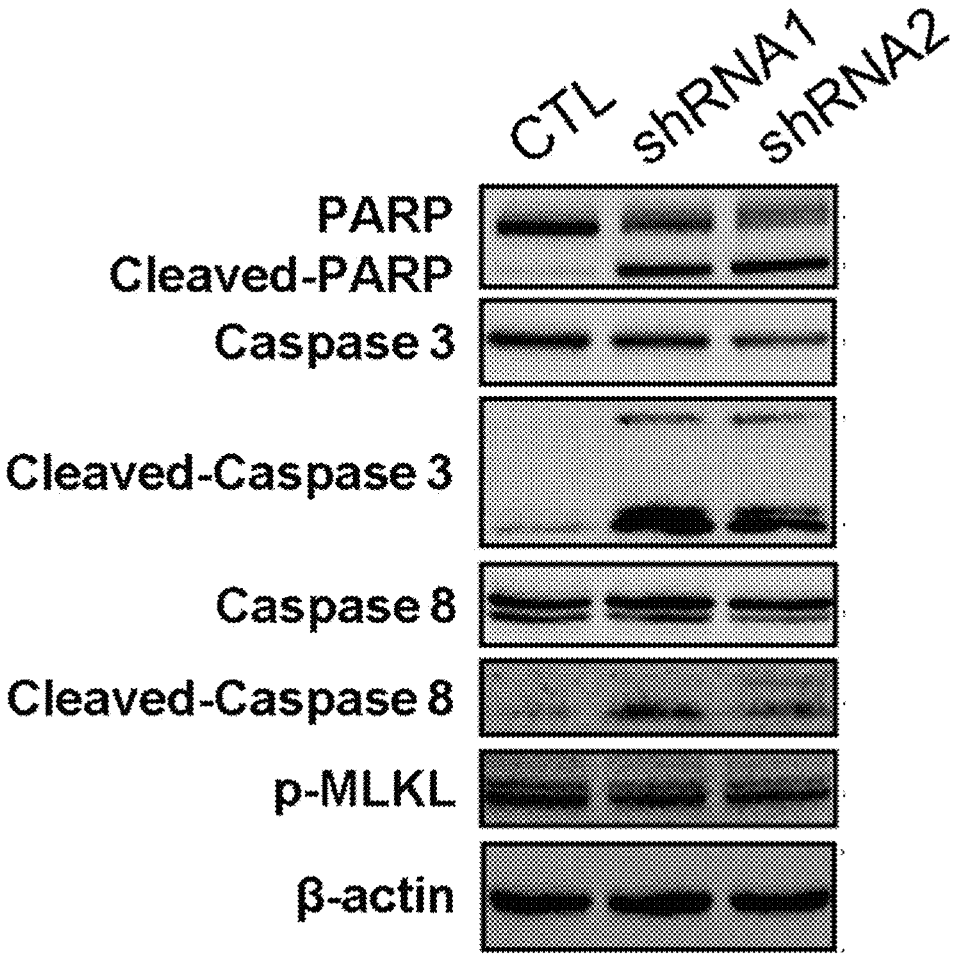
FIG. 5C is a western blot result of phosphorylation and total levels of different signaling proteins assessed by immunoblotting.

FIG. 5*b* shows the flow cytometry result of annexin-V-stained BT549 cells containing empty vector, TUBB2B shRNA1 and TUBB2B shRNA2, respectively. It illustrates that 6.72% of cells are dead in the control group, while 32.81% are dead in the BT549 cells containing shRNA1. Similarly, 40.55% of cells are dead in the BT549 cells containing shRNA2. The results demonstrate that TUBB2B deficiency induces BT549 cells apoptosis. FIG. 5C shows that the cleaved Caspases 3 and 8 are shown in the BT549 cells with TUBB2B shRNAs but not in the control group. The result indicates that TUBB2B silencing in BT549 cells induced the activation of Caspase 3 and 8.

Example 1

Preferential Overexpression of TUBB2B in TNBC

Using clinically annotated breast cancer gene expression datasets (n=310) according to Ciriello, Gatza, et al., the inventors find that whereas TUBB2B mRNA is upregulated in 3% of luminal breast tumors, its expression is significantly higher in 29% of TNBCs (FIG. 1A). Importantly, overexpression of TUBB2B is a predictor of poor distant metastasis-free survival in breast cancer patients (FIG. 1B).

Example 2 shRNAs and RNAi Molecules for Inhibiting TUBB2B Expression

A short hairpin RNA (shRNA) is an artificial RNA molecule with a tight hairpin turn that can be used to silence target gene expression via RNA interference (RNAi). The inventors prepare a series of shRNA containing RNA interference (RNAi) molecules plus other nucleotides to form a stable hairpin structure. RNAi molecules are sequences that inhibit the expression of the TUBB2B gene in a cell. The inhibition of the TUBB2B gene includes the inhibition of any fragments and isoforms of TUBB2B.

RNAi molecule includes a complementary sequence of a target sequence on an mRNA of the human TUBB2B gene. After RNAi molecules hybridize to the target sequence of TUBB2B mRNA, an RNA-induced silencing complex (RISC) will be assembled, followed by specific degradation of TUBB2B mRNA. The complementary sequence is 21 nucleotides long. 21-bp is the optimal length for loading onto the RISC, for activating the mechanism to degrade targeted mRNA, TUBB2B. In various embodiments, the 21-bp sequence is a DNA sequence selected from the group of SEQ ID NOS. 1-11.

```
SEQ ID NO. 1:
5'-ATGAAGCCACTGGTAACAAAT-3';

SEQ ID NO. 2:
5'-GATGACATCAATGTAACATTT-3';
```

-continued

```
SEQ ID NO. 3:
5'-GCTGGAGAGAATCAATGTTTA-3';

SEQ ID NO. 4:
5'-ATAAACGTTTGTGTCGGAATG-3';

SEQ ID NO. 5:
5'-AGGCACGATGGATTCGGTTAG-3';

SEQ ID NO. 6:
5'-GTCCTCTCTTTCTCTTCCTTT-3';

SEQ ID NO. 7:
5'-TCAATGTTTACTACAATGAAG-3';

SEQ ID NO. 8:
5'-AGACCAGACAATTTCGTGTTT-3';

SEQ ID NO. 9:
5'-GCAGAACAAGAACAGCAGCTA-3';

SEQ ID NO. 10:
5'-CCTGAAGATGTCGGCCACCTT-3';

SEQ ID NO. 11:
5'-CCTGAAGATGTCGGCCACCTT-3'.
```

The shRNA is a DNA molecule that includes a RNAi molecule and its reverse complementary sequence, plus necessary nucleotides. The RNAi molecules and its reverse complementary sequences targeting TUBB2B mRNA are designed based on SEQ ID NOs. 1-11. As set forth above, SEQ. ID NOS. 1-11 are DNA sequences that can be transcribed into RNA. The thymine residues in the SEQ. ID NOS. 1-11 will be transcribed uracil in RNAi molecules.

In various embodiments, the shRNA is prepared by sense oligo nucleotides and anti-sense oligonucleotides (RuiBiotech) annealed in the lab:

- shRNA prepared by sense oligo: 5'-CCGG-[RNAi molecule]-CTCGAG-[reverse complementary sequence of the previous RNAi molecule]-TTTTTG-3';
- shRNA prepared by anti-sense oligo: 5'-AATTCAAAAA [SEQ ID No. 20]-[RNAi molecule]-CTCGAG-[reverse complementary sequence of the previous RNAi molecule]-3'.

Two designed shRNAs, shRNA1 and shRNA2 are used in the below experiments.

shRNA1:

```
Sense:
                                    [SEQ ID No. 16]
CCGGATGAAGCCACTGGTAACAAATCTCG

AGATTTGTTACCAGTGGCTTCATTTTTTG;

Anti-sense:
                                    [SEQ ID No. 17]
AATTCAAAAAATGAAGCCACTGGTAACAA

ATCTCGAGATTTGTTACCAGTGGCTTCAT;

shRNA2:
Sense:
                                    [SEQ ID No. 18]
CCGGGATGACATCAATGTAACATTTCTCG

AGAAATGTTACATTGATGTCATCTTTTTG;

Anti-sense:
                                    [SEQ ID No. 19]
AATTCAAAAAGATGACATCAATGTAACAT

TTCTCGAGAAATGTTACATTGATGTCATC.
```

SEQ. ID NOS. 16 and 18, are tandem segments of both sense (SEQ. ID NO. 16) and antisense (SEQ. ID NO. 18) sequences corresponding to shRNA1. Similarly, SEQ. ID NOS. 17 and 19 (also DNA sequences) contain tandem segments of both sense (SEQ. ID NO. 17) and antisense (SEQ. ID NO. 19) sequences corresponding to shRNA2. As will be apparent to those of skill in the art, both shRNA1 and shRNA2 have a hairpin structure.

Example 3

Preparation of Lentiviral Vectors Coding shRNA

The shRNA1 and shRNA2 targeting TUBB2B mRNA are ligated to the lentiviral vector pLKO.1 or pLKO-tet-on digested by AgeI (NEB, R3552S) and EcoRI (NEB, R3101s) restriction enzyme to generate plasmids (pLKO.1-sh1/2-TUBB2B and pLKO-tet-on-sh1/2-TUBB2B). To produce lentiviral vectors, psPAX2 packaging plasmid, VSVG envelop plasmid and pLKO.1 or pLKO-tet-on or pLKO.1-sh1/2-TUBB2B or pLKO-tet-on-sh1/2-TUBB2B are co-transfected to HEK293T cells.

To prepare the DNA master mix on Day 1, 0.6 mL serum-free and antibiotic-free DMEM, 7.14 μg psPAX2 (Gag/Pol, 0.42 μg/μL), 2.38 μg VSVG (Envelope, coat proteins, 0.1 μg/μL) and 9 μg vectors carrying shRNAs-TUBB2B or empty vector are mixed together. Then, PEI (Polyethylenamine) is added to the 0.6 mL serum-free antibiotic-free DMEM. (DNA: PEI=1 μg:3 μg). The next step is gently adding the diluted PEI to the diluted DNA and gently agitating to mix them. The mixed solution is incubated at room temperature for 15 min.

The inventors trypsinize 293T cells (1 mL trypsin per 10 cm plate) and then inactivate trypsin with 9 mL (per plate) 10% FBS/DMEM (no pen/strep) before counting the number of cells. The inventors then spin down the 293T cells and resuspend cells so that cell density is adjusted to be $1\times10^7$ cells/8 mL. 8 mL cells are transferred into a 15-mL falcon tube and then mixed with the solution mentioned above. The mixture is added to 10-cm plates and incubated in a virus incubator for 48 hours. On Day 3, the inventors use a 0.45-μm filter to filter the medium containing the lentiviral vectors, make it 1-mL aliquots and store them at −80° C.

Example 4

Preparation of TUBB2B-Knockdown Cell Lines with Lentiviral Vectors

To knock down TUBB2B with pLKO.1 system, BT549 cells are seeded in 6-well plates and maintained in RPMI-1640 medium with 10% fetal bovine serum. Then cells are infected by pLKO.1 and pLKO.1-shRNA1/2-TUBB2B lentiviral vectors to silence TUBB2B mRNA. Cells are collected two days after lentivirus infection, and TUBB2B expressions are analyzed by qPCR.

To establish BT549-pLKO-tet-on and BT549-pLKO-tet-on-shRNA1/2-TUBB2B cell lines, BT549 cells are maintained in RPMI-1640 medium supplemented with 10% tet-free fetal bovine serum. BT549 cells are seeded on a 6-cm plate; then, cells are infected by the pLKO-tet-on lentiviral vectors and pLKO-tet-on-shRNA1/2-TUBB2B lentiviral vectors. To knock down the TUBB2B gene, 1×106 cells are seeded on 10-cm plates treated with or without 100 ng/ml doxycycline for 3 days. Doxycycline here is used to induce the transcription of shRNAs that can silence TUBB2B mRNA. After doxycycline treatment, cells are harvested and TUBB2B expressions are analyzed by qPCR.

In the shRNA lentiviral system for knocking down TUBB2B expression, BT549 cells are infected with TUBB2B shRNA or control (CTL) vector for 2 days, followed by RT-PCR analysis (FIG. 2A). In tet-on shRNA systems for depleting TUBB2B in BT549 tumor line, cells are treated with 100 ng/ml doxycycline for 7 days, followed by RT-PCR or Immunoblotting (FIG. 2B). FIGS. 2A and 2B show a significant depletion of TUBB2B mRNA with two distinct shRNAs in the TNBC BT549 line.

Example 5

Preparation of Gold Nanoparticles Functionalized by RNAi Molecules

Besides infection of target cells with lentiviral vectors that express RNAi molecules, RNAi molecules may, in the form of thiol-modified RNA duplexes, be delivered into the target cell (e.g., the mammalian cell), with a delivery agent. The delivery agent includes a gold nanoparticle to which RNAi molecules are bound by thiol groups, preferably through a spacer. (See, FIGS. 3 and 6)

Thiol-modified RNAi molecules, SEQ ID NO 12-15 (BGI), are shown as below. SEQ ID NO. 12 that complements SEQ ID NO. 13 corresponds to SEQ ID NO. 1. SEQ ID NO. 14 that complements SEQ ID NO. 15 corresponds to SEQ ID NO. 2.

SEQ ID NO. 12:
5'-AUGAAGCCACUGGUAACAAAU-TT $[(C_2H_{40})_6{}^-PO_3{}^-]_2$ 3'-$C_3H_6SH$

SEQ ID NO. 13:
5'-AUUUGUUACCAGUGGCUUCAU-TT 3'

SEQ ID NO. 14:
5'-GAUGACAUCAAUGUAACAUUU-TT $[(C_2H_{40})_6{}^-PO_3{}^-]_2$ 3'-$C_3H_6SH$

SEQ ID NO. 15:
5'-AAAUGUUACAUUGAUGUCAUC-TT 3'

Figure 6:
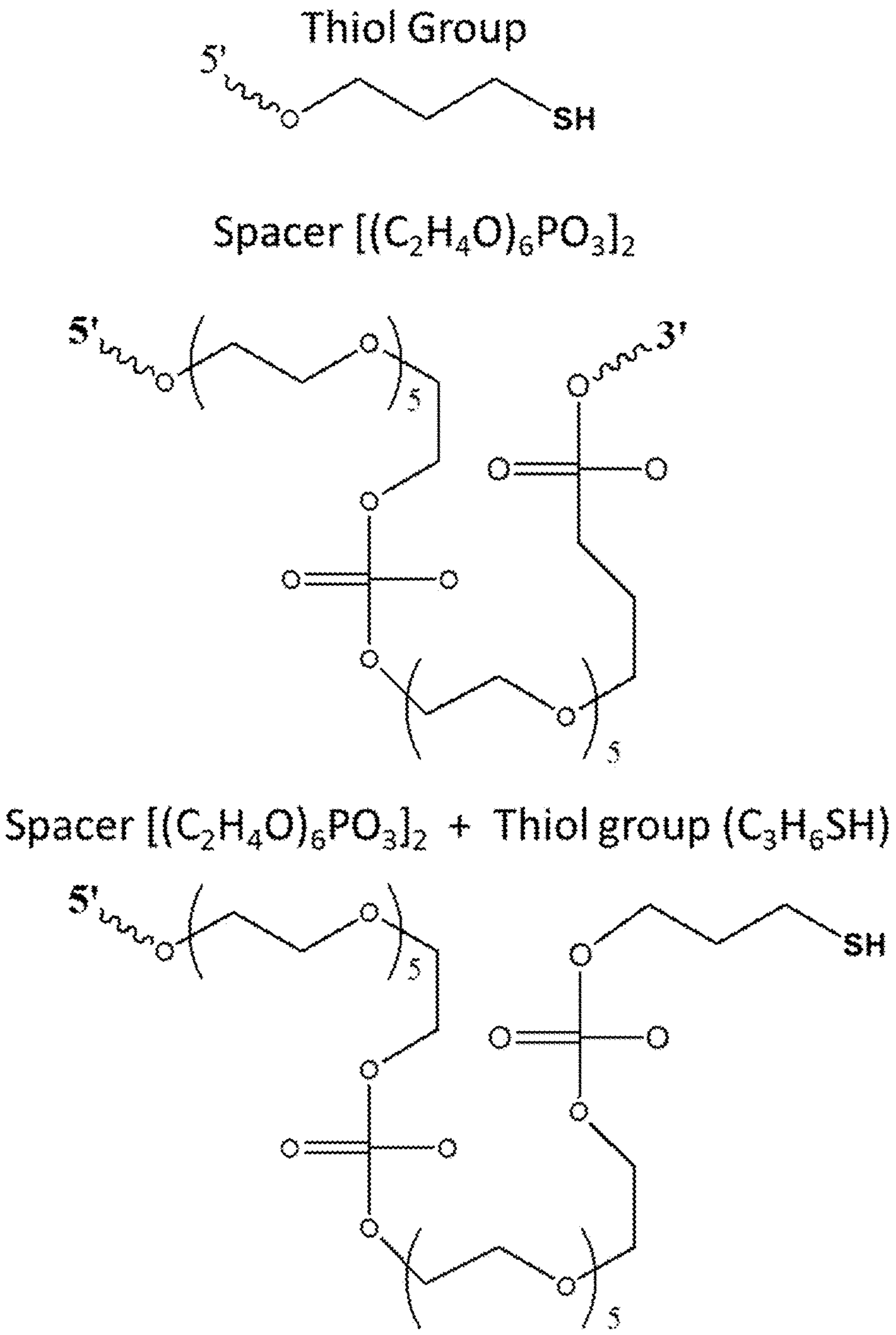
FIG. 6 shows the formulas for the thiol group, spacer, and spacer with a thiol end group according to one or more embodiments of the present invention.

In the embodiments shown in FIGS. 3 and 6, a $C_3H_6SH$ thiol group is secured to the end of the sense siRNA strands (SEQ. ID NOS. 12 and 14) by means of a $[(C_2H_4O)_6—PO_3]_2$ spacer. The spacer connects to the thiol group also via phosphodiester bonds. As will be apparent, the phosphite in these spacers is used to provide a group to form the phosphodiester bonds, akin to those between ribonucleotides. (See, FIG. 6)

Thiol-Modified RNAi molecules are annealed in an annealing buffer (30 mM Tris-HCl, 3 mM EDTA, 150 mM NaCl) at 95° C. for 10 minutes. They are left to cool slowly to room temperature to form RNA duplexes, siRNA1 and siRNA2. siRNA1 is composed of SEQ ID NO. 12 and NO. 13; And siRNA2 is composed of SEQ ID NO. 14 and NO. 15.

Then, RNA duplexes are added to RNase-free gold nanoparticles and incubated for 45 minutes at room temperature. During the incubation, RNA duplexes are allowed to chemisorb via the thiol-gold bonds. Subsequently, the concentration of NaCl is increased to 0.3 M to allow conjugation and the mixture is incubated for 16 hours at room temperature. The siRNA-functionalized gold nanoparticles are then treated with 30 μM of PEG-Thiol (PEG-SH) for 6 hours as an additional surface backfill. The unbounded agents are removed by centrifugation and the pellets are washed in RNase-free water twice. The final pellets are resuspended in phosphate buffered saline and stored at 4° ° C. The preparation process is shown in FIG. 3.

TUBB2B Plays an Essential Role in the Growth of TNBC Spheroids and Xenografts.

Example 6

The inventors perform CellTiter-Glo Luminescent Cell Viability Assay (Promega #G7571) to determine cell proliferation. BT549 or HMEC cells, infected by pLKO.1 and pLKO.1-shRNA1/2-TUBB2B lentiviral vectors for two days, are detached from plates by trypsin and resuspended in a 10% tet-free FBS RPMI-1640 medium. Then 2000 cells/well are seeded to a 96-well white polystyrene microplate (corning #3610). Three days after seeding the cells, 50 μL CellTiter Glo reagent (Promega #G7571) is added to each well and incubated at room temperature for 10 mins. Then the chemiluminescence signals are read by a multifunctional microplate reader (BioTek Synergy™ H1 Microplate Reader). The left side of FIG. 4A shows the cell viability of BT549 cells in 2D cultures, and FIG. 4B shows the cell viability of HMEC cells. Silencing TUBB2B can dramatically reduce the 2D cell viability of BT549 but has no effect on HMEC.

Example 7

Clonogenic Assay

The inventors seed 2000 cells/well of BT549 cells, infected by pLKO.1 and pLKO.1-shRNA1/2-TUBB2B lentiviral vectors for two days, to 6-well plates with 10% tet-free FBS RPMI-1640 medium refreshed every 4 days. Cells are cultured for 14 days, then fixed with 4% formaldehyde at room temperature for 10 minutes, followed by 0.1% crystal violet (in ethanol) staining for about 20 min at room temperature. The plates are washed by PBS 3 times to remove unstained crystal violet, then pictures are captured. FIG. 4C shows that the knockdown of TUBB2B inhibits the colony formation ability of BT549 cells. The result indicates that depletion of TUBB2B can lead to inhibition of BT549 colony formation.

Example 8

CellTiter-Glo 3D Cell Viability Assay (Promega #G9682) to Determine Spheroid Growth.

BT549 cells are infected by pLKO.1 and pLKO.1-shRNA1/2-TUBB2B lentiviral vectors for two days. Then cells are resuspended in assay medium (10% tet-free FBS RPMI-1640 containing 2% Matrigel) and seeded into to 96-well white polystyrene microplate (corning #3610) pre-coated with Matrigel (corning #354230), 1500 cells/well. The assay medium is refreshed every 4 days. Pictures are captured using a phase-contrast microscope seven days after cells are seeded. The spheroid size and density of BT549 knocked-down TUBB2B are markedly decreased. To detect the 3D spheroids viability, 100 μL 3D CellTiter Glo reagent (Promega #G9682) is added to each well and incubated at room temperature for 15 mins. Then the chemiluminescence signals are read by a multifunctional microplate reader (BioTek Synergy™ H1 Microplate Reader). FIG. 4D shows that TUBB2B knockdown decreases the 3D-spheroid cell viability and growth of BT549 cells.

Example 9

Xenograft Experiment

Six-week-old female nude mice are purchased from the Laboratory Animal Research Unit, City University of Hong Kong. Mice are randomly grouped into 2 groups of 5 mice. 10 μg lentiviral vectors (pLKO.1 and pLKO.1-shRNA1-TUBB2B) are co-transfected with 7 μg psPAX2 (Addgene, 12260) and 2.4 μg VSV-G (Addgene, 12259) vectors to HEK293T cells (ATCC) cultured in 10-cm plates, using polyethylenimine as transfection reagent. Lentiviral supernatant (~10 ml) is filtered by a 0.45 μm filter (Thermo fisher, 7232545). MDA-MB-468 cells (ATCC) are seeded onto 15-cm plates, then infected with pLKO.1 and pLKO.1-shRNA1-TUBB2B lentiviral vectors (2.7 mL of lentiviral supernatant) for two days. Then, trypsin (Trypsin-EDTA 0.25%, Thermo fisher, 25200114) is used to detach cells. Cells are collected and counted, followed by three times PBS washing. Then cells are resuspended by 50% Matrigel (Corning #356237) in PBS to make the cell density 5×105 cells/100 μL. Cells are injected into the mammary fat pad of nude mice to form a tumor. Each injection contains 5×105 cells. Tumor size is measured every 2-3 days.

In mouse pre-clinical models, an injection of $5\times10^8$ transduction units per mouse intravenously can achieve a good expression of the target. (Van den Brand B T, Vermeij E A, Waterborg C E, et al., 2013)

For use in humans, the lentiviral vectors are injected into the tumor site to infect the cancer cells inside the body. Milone et al. (2018) have reviewed the successful use of lentiviral vectors for cancer therapy. Injection in situ of $2.4\times10^4$-$8.0\times10^5$ transduction units of lentiviral vectors in humans is well-tolerated with no-limiting toxicities. In humans, patients with advanced cancer received $1\times10^8$-$1\times10^{10}$ transduction units by intradermal injection with no dose-limiting toxicities observed. (Somaiah N, Block M S, Kim J W, et al., 2019) In a preferred embodiment, RNAi molecules can be bound to gold nanoparticles described in Example 5, and the RNAi-gold nanoparticles are injected into a subject intravenously.

TUBB2B silencing results in potent inhibition of TNBC viability in 2D cultures and colony formation in a clonogenic assay (FIGS. 4A-4C). Importantly, TUBB2B depletion does not affect the viability of normal human mammary epithelial cells (HMEC) (FIG. 4B), indicating the potential to target TUBB2B for therapeutic purposes. Our data also demonstrates that depletion of TUBB2B in TNBC cells potently inhibits 3D spheroid growth (FIG. 4D). In pre-clinical studies (FIG. 4E), the results show that TUBB2B depletion significantly inhibits TNBC xenograft growth. FIG. 4E shows that knocking down TUBB2B in MDA-MB-468 can lead to a significant decrease in tumor size.

TUBB2B Depletion Induces Apoptosis of Breast Cancer Cells

Example 10

PI and Annexin V Staining

Three days after BT549 cells are infected by pLKO.1 and pLKO.1-shRNA1/2-TUBB2B lentiviral vectors. The adherent and suspended cells are trypsinized and counted. For Propidium Iodide (PI) staining, 50×104 cells are taken and spun down at 2000 rpm for 4 minutes at room temperature. After discarding the medium, the remaining is washed once with cold PBS and resuspended in 1 mL PBS. The full volume of the resuspended cells is transferred to 4 mL of absolute ethanol and put at −20° C. overnight. The next day, the cells are spun down at 1200 rpm for 5 minutes to discard ethanol. Then 0.5 mL PBS with 0.1% Nonidet P-40, 1 g/mL RNase and 1:500 PI (life technologies: P3566) are added. The cells are resuspended and incubated at room temperature for 30 minutes. Then it follows with flow cytometry for analysis. FIG. 5A shows the cell cycles of BT549 with control and knockdown TUBB2B. TUBB2B knockdown has minimal effect on cell cycle phase distribution.

For annexin V staining, 50×104 cells are taken and spun down at 2000 rpm for 4 minutes at room temperature. After discarding the medium, the remaining is washed by 1× binding buffer once and the binding buffer is discarded. 0.25 mL of 1× binding buffer and 2.5 μL Annexin V-PE/Cy7 (Life Technologies, 88-8103-72) are added to each sample. The samples are incubated at room temperature for 15 mins, then spun down cells at 2000 rpm for 4 minutes. The supernatant is discarded. The cells are resuspended with 0.4 mL 1× binding buffer. The Annexin V-PE/Cy7 signal is analyzed by flow cytometry. FIG. 5B shows that TUBB2B deficiency induces apoptosis of BT549 cells.

Example 11

Western Blot

BT549 cells, 3 days after infection of pLKO.1 and pLKO.1-shRNA1/2-TUBB2B lentiviral vectors, are washed with PBS at 4° C. and lysed in EBC buffer (0.5% NP-40, 120 mM NaCl, 50 mM Tris-HCl (pH 7.4), proteinase inhibitor cocktail, 50 nM calyculin, 1 mM sodium pyrophosphate, 20 mM sodium fluoride and 2 mM EDTA, 2 mM EGTA) for 30 min on ice. Cell extracts are pre-cleared by centrifugation at a relative centrifugal force of 13,000×g for 10 min at 4° C. and the concentration of the protein is measured with the Bio-Rad protein assay reagent using a BioTek Synergy™ H1 Microplate Reader. Lysates are then resolved on 12% acrylamide gels by SDS-PAGE and transferred electrophoretically to nitrocellulose membrane (Bio-Rad) at 280 mA for 80 min. The blots are blocked in TBST buffer (10 mM Tris-HCl, pH 8, 150 mM NaCl, 0.2% Tween 20) containing 5% (w/v) non-fat dry milk for 30 min, and then incubated with the specific primary antibody diluted in blocking buffer at 4° C. overnight. Membranes are washed three times in TBST and incubated with horseradish peroxidase-conjugated secondary antibody for 1 hour at room temperature. Membranes are washed three times and developed using enhanced chemiluminescence substrate (Pierce). FIG. 5C shows that TUBB2B silencing in BT549 cells induced the activation of Caspase 3 and 8.

Interestingly, TUBB2B knockdown has minimal effect on cell cycle progression (FIG. 4A), indicating that mitotic catastrophe is unlikely to be the cell death mechanism. Our data showed that TUBB2B silencing induced TNBC cell apoptosis (FIG. 4B), accompanied by the activation of Caspase 3 and 8 (FIG. 4C). These data point to RNAi molecules against TUBB2B as a novel therapeutic strategy for TNBC, particularly for tumors overexpressing TUBB2B.

Without intending to be limited by theory, it is believed that TUBB2B knockout by RNAi molecules in treating a cancer or a tumor can be used in combination with other cancer therapies or drugs. A potential combination would include, but not limited to, PI3K/Akt pathway inhibitors, CDK4/6 inhibitors, and MEK inhibitors. Also, TUBB2B knockout by RNAi molecules and chemotherapy, such as chemotherapeutic agents (paclitaxel, cisplatin, etc.), can be applied in combination.

It should be understood that the above only illustrates and describes examples whereby the present invention may be carried out, and that modifications and/or alterations may be made thereto without departing from the spirit of the invention.

It should also be understood that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

All references specifically cited herein are hereby incorporated by reference in their entireties. However, the citation or incorporation of such a reference is not necessarily an admission as to its appropriateness, applicability, and/or availability as prior art to/against the present invention.

What is claimed is:

1. A short hairpin RNA (shRNA) for inhibiting TUBB2B expression, encoded by a DNA sequence comprising, from 5' to 3':

(a) a RNAi sequence that hybridizes to a target sequence on an mRNA of TUBB2B gene;

(b) a CTCGAG sequence for forming a loop of the shRNA; and (c) a reverse complementary sequence of said RNAi sequence;

wherein the RNAi sequence is selected from the group consisting of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, and SEQ ID NO. 11.

2. A method of inhibiting TUBB2B expression, comprising the step of administering a shRNA according to claim 1 to a cell.

3. The method according to claim 2, wherein the administration step is performed by introducing a lentiviral vector expressing the shRNA in the cell.

4. The method according to claim 3, wherein the lentiviral vectors comprises a sequence that encodes the shRNA and a suitable promoter for expressing the shRNA.

5. The method according to claim 2, wherein the cell is a mammalian cell.

6. The method according to claim 2, wherein the administration step comprises administering gold nanoparticles functionalized by a RNAi molecule, wherein the RNAi molecule comprises a siRNA sequence selected from the group consisting of SEQ ID NO. 12, SEQ ID NO. 13, SEQ ID NO. 14, and SEQ ID NO. 15.

7. A method of treating or controlling a cancer mediated by TUBB2B overexpression, comprising the step of administering an effective amount of a shRNA according to claim 1 to a subject, wherein the cancer is triple-negative breast cancer.

8. The method according to claim 7, wherein the administration step is performed by injecting a lentiviral vector that expresses the shRNA therein into the subject.

9. The method according to claim 7, wherein the administration step comprises administering gold nanoparticles functionalized by a RNAi molecule, wherein the RNAi molecule comprises a siRNA sequence selected from the group consisting of SEQ ID NO. 12, SEQ ID NO. 13, SEQ ID NO. 14, and SEQ ID NO. 15.

10. A pharmaceutical composition comprising the shRNA according to claim 1.

11. The pharmaceutical composition according to claim 10, further comprising an effective amount of an additional agent selected from the group consisting of a PI3K/Akt pathway inhibitor, a CDK4/6 inhibitor, a MEK inhibitor, a chemotherapeutical agent, and a combination thereof.

12. The short hairpin RNA (shRNA) according to claim 1, wherein the shRNA is prepared by annealing a sense oligo and an anti-sense oligo:

(a) Sense oligo: 5'-CCGG-RNAi sequence-CTCGAG-reverse complementary sequence of said RNAi sequence-TTTTTG-3', and (b) Anti-sense oligo: 5'-AATTCAAAAA [SEQ ID No. 20]-RNAi sequence-CTCGAG-reverse complementary sequence of said RNAi sequence-3', wherein the RNAi sequence hybridizes to a target sequence on an mRNA of TUBB2B gene and is selected from the group consisting of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, and SEQ ID NO. 11.

* * * * *

SEQUENCE LISTING

```
Sequence total quantity: 20
SEQ ID NO: 1             moltype = DNA  length = 21
FEATURE                  Location/Qualifiers
source                   1..21
                         mol_type = other DNA
                         organism = unidentified
misc_feature             1..21
                         function = Segment is transcribed into an interfering RNA
                          (RNAi) segment that hybridizes to a target sequence on an
                          mRNA of TUBB2B gene to block expression of the TUBB2B gene.
SEQUENCE: 1
atgaagccac tggtaacaaa t                                                    21

SEQ ID NO: 2             moltype = DNA  length = 21
FEATURE                  Location/Qualifiers
source                   1..21
                         mol_type = other DNA
                         organism = synthetic construct
misc_feature             1..21
                         function = Segment is transcribed into an interfering RNA
                          (RNAi) segment that hybridizes to a target sequence on an
                          mRNA of TUBB2B gene to block expression of the TUBB2B gene.
SEQUENCE: 2
gatgacatca atgtaacatt t                                                    21

SEQ ID NO: 3             moltype = DNA  length = 21
FEATURE                  Location/Qualifiers
source                   1..21
                         mol_type = other DNA
                         organism = synthetic construct
misc_feature             1..21
                         function = Segment is transcribed into an interfering RNA
                          (RNAi) segment that hybridizes to a target sequence on an
                          mRNA of TUBB2B gene to block expression of the TUBB2B gene.
SEQUENCE: 3
gctggagaga atcaatgttt a                                                    21

SEQ ID NO: 4             moltype = DNA  length = 21
FEATURE                  Location/Qualifiers
source                   1..21
                         mol_type = other DNA
                         organism = synthetic construct
misc_feature             1..21
                         function = Segment is transcribed into an interfering RNA
                          (RNAi) segment that hybridizes to a target sequence on an
                          mRNA of TUBB2B gene to block expression of the TUBB2B gene.
SEQUENCE: 4
ataaacgttt gtgtcggaat g                                                    21

SEQ ID NO: 5             moltype = DNA  length = 21
FEATURE                  Location/Qualifiers
source                   1..21
                         mol_type = other DNA
                         organism = synthetic construct
misc_feature             1..21
                         function = Segment is transcribed into an interfering RNA
                          (RNAi) segment that hybridizes to a target sequence on an
                          mRNA of TUBB2B gene to block expression of the TUBB2B gene.
SEQUENCE: 5
aggcacgatg gattcggtta g                                                    21

SEQ ID NO: 6             moltype = DNA  length = 21
FEATURE                  Location/Qualifiers
source                   1..21
                         mol_type = other DNA
                         organism = synthetic construct
misc_feature             1..21
                         function = Segment is transcribed into an interfering RNA
                          (RNAi) segment that hybridizes to a target sequence on an
                          mRNA of TUBB2B gene to block expression of the TUBB2B gene.
```

```
SEQUENCE: 6
gtcctctctt tctcttcctt t                                            21

SEQ ID NO: 7           moltype = DNA  length = 21
FEATURE                Location/Qualifiers
source                 1..21
                       mol_type = other DNA
                       organism = synthetic construct
misc_feature           1..21
                       function = Segment is transcribed into an interfering RNA
                        (RNAi) segment that hybridizes to a target sequence on an
                        mRNA of TUBB2B gene to block expression of the TUBB2B gene.
SEQUENCE: 7
tcaatgttta ctacaatgaa g                                            21

SEQ ID NO: 8           moltype = DNA  length = 21
FEATURE                Location/Qualifiers
source                 1..21
                       mol_type = other DNA
                       organism = synthetic construct
misc_feature           1..21
                       function = Segment is transcribed into an interfering RNA
                        (RNAi) segment that hybridizes to a target sequence on an
                        mRNA of TUBB2B gene to block expression of the TUBB2B gene.
SEQUENCE: 8
agaccagaca atttcgtgtt t                                            21

SEQ ID NO: 9           moltype = DNA  length = 21
FEATURE                Location/Qualifiers
source                 1..21
                       mol_type = other DNA
                       organism = synthetic construct
misc_feature           1..21
                       function = Segment is transcribed into an interfering RNA
                        (RNAi) segment that hybridizes to a target sequence on an
                        mRNA of TUBB2B gene to block expression of the TUBB2B gene.
SEQUENCE: 9
gcagaacaag aacagcagct a                                            21

SEQ ID NO: 10          moltype = RNA  length = 21
FEATURE                Location/Qualifiers
source                 1..21
                       mol_type = other RNA
                       organism = synthetic construct
misc_feature           1..21
                       function = Segment is transcribed into an interfering RNA
                        (RNAi) segment that hybridizes to a target sequence on an
                        mRNA of TUBB2B gene to block expression of the TUBB2B gene.
SEQUENCE: 10
cctgaagatg tcggccacct t                                            21

SEQ ID NO: 11          moltype = DNA  length = 21
FEATURE                Location/Qualifiers
source                 1..21
                       mol_type = other DNA
                       organism = synthetic construct
misc_feature           1..21
                       function = Segment is transcribed into an interfering RNA
                        (RNAi) segment that hybridizes to a target sequence on an
                        mRNA of TUBB2B gene to block expression of the TUBB2B gene.
SEQUENCE: 11
cctgaagatg tcggccacct t                                            21

SEQ ID NO: 12          moltype = RNA  length = 23
FEATURE                Location/Qualifiers
source                 1..23
                       mol_type = other RNA
                       organism = synthetic construct
misc_binding           23
                       bound_moiety = -[(C2H4O)6PO3]2C3H6SH
misc_RNA               1..21
                       function = hybridizes to a target sequence on an mRNA of
                        TUBB2B gene to block expression of the TUBB2B gene
                       note = RNA interference (RNAi) molecule
modified_base          22..23
                       mod_base = OTHER
                       note = thymine residue
SEQUENCE: 12
atgaagccac tggtaacaaa ttt                                          23
```

```
SEQ ID NO: 13          moltype = RNA  length = 23
FEATURE                Location/Qualifiers
source                 1..23
                       mol_type = other RNA
                       organism = synthetic construct
misc_RNA               1..21
                       function = hybridizes to a target sequence on an mRNA of
                        TUBB2B gene to block expression of the TUBB2B gene
                       note = RNA interference (RNAi) molecule
modified_base          22..23
                       mod_base = OTHER
                       note = thymine residue
SEQUENCE: 13
atttgttacc agtggcttca ttt                                          23

SEQ ID NO: 14          moltype = RNA  length = 23
FEATURE                Location/Qualifiers
source                 1..23
                       mol_type = other RNA
                       organism = synthetic construct
misc_binding           23
                       bound_moiety = -[(C2H4O)6PO3]2C3H6SH
misc_RNA               1..21
                       function = hybridizes to a target sequence on an mRNA of
                        TUBB2B gene to block expression of the TUBB2B gene
                       note = RNA interference (RNAi) molecule
modified_base          22..23
                       mod_base = OTHER
                       note = thymine residue
SEQUENCE: 14
gatgacatca atgtaacatt ttt                                          23

SEQ ID NO: 15          moltype = RNA  length = 23
FEATURE                Location/Qualifiers
source                 1..23
                       mol_type = other RNA
                       organism = synthetic construct
misc_RNA               1..21
                       function = hybridizes to a target sequence on an mRNA of
                        TUBB2B gene to block expression of the TUBB2B gene
                       note = RNA interference (RNAi) molecule
modified_base          22..23
                       mod_base = OTHER
                       note = thymine residue
SEQUENCE: 15
aaatgttaca ttgatgtcat ctt                                          23

SEQ ID NO: 16          moltype = DNA  length = 58
FEATURE                Location/Qualifiers
source                 1..58
                       mol_type = other DNA
                       organism = synthetic construct
misc_feature           5..25
                       function = hybridizes to a target sequence on an mRNA of
                        TUBB2B gene to block expression of the TUBB2B gene
                       note = Interfering RNA (RNAi) segment
stem_loop              1..58
                       note = sense short hairpin RNA (shRNA) segment
misc_feature           32..52
                       note = reverse complementary segment of residues 5..25
SEQUENCE: 16
ccggatgaag ccactggtaa caaatctcga gatttgttac cagtggcttc attttttg    58

SEQ ID NO: 17          moltype = DNA  length = 58
FEATURE                Location/Qualifiers
source                 1..58
                       mol_type = other DNA
                       organism = synthetic construct
misc_feature           1..58
                       note = anti-sense short hairpin RNA (shRNA) segment
stem_loop              11..31
                       note = Forms hairpin structure with residues 38..58
stem_loop              38..58
                       note = Forms hairpin structure with residues 11..31
SEQUENCE: 17
aattcaaaaa atgaagccac tggtaacaaa tctcgagatt tgttaccagt ggcttcat    58
```

-continued

```
SEQ ID NO: 18          moltype = DNA  length = 58
FEATURE                Location/Qualifiers
source                 1..58
                       mol_type = other DNA
                       organism = synthetic construct
stem_loop              1..58
                       note = sense short hairpin RNA (shRNA) segment
misc_feature           5..25
                       function = hybridizes to a target sequence on an mRNA of
                        TUBB2B gene to block expression of the TUBB2B gene
                       note = Interfering RNA (RNAi) segment
misc_feature           32..52
                       note = reverse complementary segment of residues 5..25
SEQUENCE: 18
ccgggatgac atcaatgtaa catttctcga gaaatgttac attgatgtca tctttttg    58

SEQ ID NO: 19          moltype = DNA  length = 58
FEATURE                Location/Qualifiers
source                 1..58
                       mol_type = other DNA
                       organism = synthetic construct
misc_feature           1..58
                       note = anti-sense short hairpin RNA (shRNA) segment
stem_loop              11..31
                       note = Forms hairpin structure with residues 38..58
stem_loop              38..58
                       note = Forms hairpin structure with residues 11..31
SEQUENCE: 19
aattcaaaaa gatgacatca atgtaacatt tctcgagaaa tgttacattg atgtcatc    58

SEQ ID NO: 20          moltype = DNA  length = 10
FEATURE                Location/Qualifiers
source                 1..10
                       mol_type = other DNA
                       organism = synthetic construct
SEQUENCE: 20
aattcaaaaa                                                         10
```